United States Patent
Rynerson

(10) Patent No.: US 10,799,447 B2
(45) Date of Patent: Oct. 13, 2020

(54) METHOD OF TREATING AN EYE DISORDER BY INHIBITING OR DISRUPTING BACTERIAL BIOFILM FORMATION

(71) Applicant: James M. Rynerson, Franklin, TN (US)

(72) Inventor: James M. Rynerson, Franklin, TN (US)

( * ) Notice: Subject to any disclaimer, the term of this patent is extended or adjusted under 35 U.S.C. 154(b) by 23 days.

(21) Appl. No.: 16/082,151

(22) PCT Filed: Mar. 3, 2017

(86) PCT No.: PCT/US2017/020618
§ 371 (c)(1),
(2) Date: Sep. 4, 2018

(87) PCT Pub. No.: WO2017/152027
PCT Pub. Date: Sep. 8, 2017

(65) Prior Publication Data
US 2019/0091142 A1 Mar. 28, 2019

Related U.S. Application Data

(60) Provisional application No. 62/304,033, filed on Mar. 4, 2016, provisional application No. 62/304,024, filed on Mar. 4, 2016.

(51) Int. Cl.
| | | |
|---|---|---|
| A61K 39/00 | (2006.01) | |
| A61K 39/395 | (2006.01) | |
| A61K 49/00 | (2006.01) | |
| A61K 9/00 | (2006.01) | |
| A61K 35/66 | (2015.01) | |
| A61K 33/00 | (2006.01) | |
| C07K 16/12 | (2006.01) | |
| A61K 38/16 | (2006.01) | |
| A61K 38/22 | (2006.01) | |
| A61K 38/40 | (2006.01) | |
| A61K 36/185 | (2006.01) | |
| A61K 38/39 | (2006.01) | |
| A61K 31/4035 | (2006.01) | |
| A61K 31/5377 | (2006.01) | |
| A61K 31/4725 | (2006.01) | |
| A61K 31/352 | (2006.01) | |
| A61K 31/047 | (2006.01) | |

(52) U.S. Cl.
CPC .......... *A61K 9/0048* (2013.01); *A61K 31/047* (2013.01); *A61K 31/352* (2013.01); *A61K 31/4035* (2013.01); *A61K 31/4725* (2013.01); *A61K 31/5377* (2013.01); *A61K 33/00* (2013.01); *A61K 35/66* (2013.01); *A61K 36/185* (2013.01); *A61K 38/164* (2013.01); *A61K 38/2292* (2013.01); *A61K 38/39* (2013.01); *A61K 38/40* (2013.01); *A61K 39/395* (2013.01); *C07K 16/12* (2013.01); *C07K 16/1267* (2013.01); *C07K 2317/76* (2013.01)

(58) Field of Classification Search
CPC ....... A61K 49/00; A61K 39/00; A61K 39/395
USPC ...... 424/9.1, 9.2, 130.1, 164.1, 184.1, 234.1
See application file for complete search history.

(56) References Cited

U.S. PATENT DOCUMENTS
4,894,221 A    1/1990  Hernestam et al.

FOREIGN PATENT DOCUMENTS
| CA | 2670409 A1 | 5/2008 |
| WO | WO2008127099 | * 10/2008 |
| WO | 2012118535 A1 | 9/2012 |

OTHER PUBLICATIONS

Lam et al. infection and Immunity, 82(9):3764-3774, Sep. 2014.*
Berkes et al. WO2012/118535 A1, Sep. 7, 2012.*
Boles, Blaise R. et al., "Staphylococcal biofilm disassembly", Trends in Microbiology, retrieved Jun. 22, 2011, pp. 449-455, vol. 19, No. 9.
Lam, H. et al. "Antibodies to PHnD Inhibit Staphylococcal Biofilms", Infection and Immunity, Sep. 1, 2014, pp. 3764-3774, vol. 82, No. 9.
Rabin, Nira et al., "Agents that inhibit bacterial biofilm formation", Future Medicinal Chemistry, Apr. 1, 2015, pp. 647-671, vol. 7, No. 5.
International Searching Authority, International Search Report and Written Opinion issued in related case PCT/US2017/020618, dated May 23, 2017, 15 pages.

* cited by examiner

*Primary Examiner* — Rodney P Swartz
(74) *Attorney, Agent, or Firm* — Wood Herron & Evans LLP

(57) ABSTRACT

The present invention relates to methods of treating blepharitis and dry eye by inhibiting the binding ability of lid flora bacteria such as *Staphylococcus aureus* and *Staphylococcus epidermidis,* thus inhibiting biofilm formation and the increase in bacterial populations and densities that lead to quorum-sensing-gene activation and therefore, the production of inflammatory virulence factors.

5 Claims, No Drawings

METHOD OF TREATING AN EYE DISORDER BY INHIBITING OR DISRUPTING BACTERIAL BIOFILM FORMATION

FIELD

The present invention relates to methods and compositions for treating an eye disorder, and more particularly, to methods and compositions of treating an eye disorder by inhibiting or disrupting biofilm formation on an aspect of the eye.

BACKGROUND

Dry Eye and Blepharitis Syndrome (DEBS) has historically been thought of as a multifactorial disease of tear quantity and quality resulting in disruption of the ocular and conjunctival surfaces resulting in symptoms of irritation and dryness as well as visual disturbances and fluctuations in vision. Damage to the ocular, lid margin and conjunctival surfaces can be the long term result of DEBS.

DEBS is probably the most common eye disease in the world, and unfortunately, one of the most poorly understood and under-treated eye diseases of our time. There is no single diagnostic test for DEBS and therefore the exact prevalence of this disease is difficult to determine. Most prevalence studies have failed to recognize blepharitis and dry eye disease as differing stages of the same disease process, and thus there is a significant amount of overlap when evaluating the prevalence of this disease. Based on the self-reporting of dry eyes in the Beaver Dam Offspring cohort, the prevalence of dry eye was 14.5 percent (17.9 percent in women and 10.5 percent in men). Other studies have estimated dry eye prevalence at 5 to 30 percent of the population age 50 years and over. Self-reporting is a poor protocol for estimating dry eye disease, because early meibomian gland disease is often asymptomatic. Studies on blepharitis prevalence have focused on doctor reporting, thereby evaluating their existing patient populations to determine prevalence. This method is obviously skewed towards patients already under the care of an eye doctor, so would pre-select towards patients with existing symptoms. These numbers range from 40% to 65%. The complexity of overlapping symptoms makes determination difficult as well. When factoring the number of contact lens wearers in the US, currently around 40 million, it is easy to see that DEBS is a significant eye problem worldwide, with a need for better understanding and treatment of this chronic disease.

In order to understand the complexities of presentation of this disease, many have attempted to classify dry eye and blepharitis into sub-categories such as anterior blepharitis, posterior blepharitis, staphylococcal blepharitis, seborrheic blepharitis, evaporative dry eye disease, aqueous insufficiency dry eye, and autoimmune dry eye disease such as Sjogrens disease, among others. While autoimmune disease is certainly a class of disease unto itself, which is manifested as inflammation emanating from within the body, the vast majority of dry eye disease is age or contact lens wear related and not associated with a systemic autoimmune process. Therefore, it must be considered to be inflammation from an exogenous source from the eyelid margin, in an otherwise healthy individual. Attempts to classify dry eye and blepharitis as anterior blepharitis, posterior blepharitis, staphylococcal blepharitis, seborrheic blepharitis, evaporative dry eye disease, aqueous insufficiency dry eye as separate disease entities, are one of the main reasons that has hampered understanding and treatment of these diseases. It is axiomatic in medicine that a multitude of symptoms in a patient are better explained, not by a multitude of diseases, but by one disease process that can explain and account for a multitude of symptoms and presentations.

It is well accepted that dry eye and blepharitis are inflammatory-based diseases. Indeed, a prominent eye drop medication, Restasis® is based on suppressing existing inflammation. A better approach would be to identify a source of inflammation that can account for the many presentations of DEBS. In doing so, the nature of this disease may be better understood and better treatment options may be formulated to address the source of inflammation. There exists a need for a medication that addresses the source of inflammation thereby preventing inflammation from occurring in the first place.

Historically, blepharitis has been treated by advising patients to perform home lid hygiene regimes, which are ineffective and difficult for most patients to do. There is a multitude of home lid hygiene products such as surfactant-based lid wipes, hypochlorous acid and warm compresses. Dry eye disease treatments have been mostly ameliorative, with a multitude of various artificial tears on the market, and more recently, in-office treatments such as Lipiflow®, Meiboflow®, manual meibomian gland expression, and BlephEx®, which is an in-office treatment that allows doctors to completely remove lid margin biofilms. None of these treatments address a recurrence of the source of inflammation, and must be repeated at regular intervals.

DETAILED DESCRIPTION

Aspects of the present invention are directed to methods and compositions for treating Dry Eye and Blepharitis Syndrome (DEBS) based a better understanding of this complex syndrome that comes from understanding the nature of the normal lid flora bacteria, primarily *Staphylococcus aureus* and *Staphylococcus epidermidis*. Bacteria in nature do not typically live in a planktonic state, i.e. free-floating, but rather form a biofilm matrix of protein and polysaccharide, which, when formed on structures in and around the eye can result in indiscriminate, exogenous inflammatory lid disease. Treatments that prevent the build-up of biofilm on eye structure thereby eliminating or reducing the source of inflammation, such as with an easy to administer eye drop medication, would be favorable to attempting to ameliorate, the late sequela of inflammatory dry eye disease with artificial tears, or preventing the activation of lymphocytes with an integrin antagonist, or even removing the biofilm mechanically with a BlephEx® device.

Biofilms are complex structures produced by virtually all bacteria and are the prevailing microbial lifestyle seen in nature. Biofilms may occur anywhere in nature where there exists a combination of moisture, nutrients and a surface. The eyelid margin is a perfect example of this type of environment. The biofilm is initiated by the binding of the bacteria to a surface, such as an epithelial cell, or the fibronectin inherent in human tears, and facilitated by a protein molecule called an adhesin. Once adherent, the bacteria manufacture the protein and polysaccharide components of the biofilm which is inherently sticky and also binds tightly to the surface. This biofilm continues to accumulate on the margin of the eyelid throughout the years of an individual's life, eventually allowing the densities and populations of bacteria to increase dramatically. The biofilm allows the bacteria to resist antibiotics and avoid the host's defense mechanisms, effectively sheltering in place. Once the population reaches a critical point, quorum-sensing gene activation occurs activating dormant bacterial genes to begin producing highly inflammatory virulence factors such as cytolytic toxins, enzymes, more adhesins, and exotoxins. Without being bound to any particular theory, these virulence factors that are primarily responsible for the various inflammatory manifestations of lid margin disease.

Further confusion of this disease is due to the failure to recognize that the multiple manifestations of lid margin disease that are seen clinically are simply different stages of the same inflammatory process. Whereas most diseases present their manifestations and symptoms at the same time or within a relatively short time frame, making the examiner search for one disease, the symptoms and manifestations of DEBS occur and progress through stages over a course of decades, with the later stages typically masking manifestations of the earlier stages, although they typically still exist. This lack of immediate concurrence leads the practitioner to think he/she is seeing a different disease process. If one starts with the concept of bacterial/biofilm mediated inflammation lid margin disease, the differing stages of disease can then be explained simply through anatomical variations and locations of the involved tissue.

Stage 1 DEBS involves the follicles of the lashes because of a very close proximity to the surface biofilm virulence factors, and a relatively easy journey down the shaft of the eyelash itself. Once the biofilm, virulence factors or both the biofilm and virulence factors are within the lash follicle, folliculitis ensues with slight swelling of the follicle and tissue surrounding the eyelash. This early stage of DEBS development is typically asymptomatic and frequently goes unnoticed. As biofilm material accumulates within the lash follicles, this stage of DEBS is commonly diagnosed as "anterior blepharitis" based on visualizing "scurf/debris/dandruff" on the eyelashes. The "debris" is actually comprised of small chunks or collarettes of biofilm that have been pulled off of the lid margin by still healthy and growing eyelashes, and is typically the first outward appearance that is appreciated by the examiner. However, the literal meaning of the word "blepharitis" implies "lid inflammation". As such, "debris" on the inert, non-inflammable eyelashes, while evidence of an existing biofilm and the potential inflammatory process it represents, should not be, by itself, a clinical sign sufficient to cover the entire disease process called "blepharitis." Thus, using the term "blepharitis" to diagnose a lid disorder at this stage would require broadening the use of this term to encompass other manifestations of actual lid inflammation that may or may not include lash debris. This is what the term "posterior blepharitis" was meant to address. This term, however, implies that meibomian inflammation is a separate disease and fails to recognize the staged disease process that will involve other structures later in the inflammatory process. Within later stages of inflammation, the follicles will still be inflamed, many times to the point of lash misdirection, poor growth or actual lash loss, but without debris in the lash line due to the poor growth of the lash.

Stage 2 DEBS involves inflammation and degradation of the meibomian glands resulting in a loss of the lipid layer of the tear film, and therefore, evaporative dry eye disease. This is commonly referred to as posterior blepharitis, making a distinction from follicular or anterior involvement, and implying a separate disease. Also, the impressive clinical picture of inflamed meibomian glands and the prominent symptoms of irritation, poor vision and evaporative dry eye masks the now, minor findings of follicular edema, so anterior involvement is often overlooked. If one were to examine closely, one would find edema of the follicles in nearly every case of meibomian inflammation, thus illustrating the staged nature of this disease. Meibomian disease occurs after follicular disease because of the anatomy and location of the meibomian glands. The gland itself is 1,000 times larger than the lash follicle, so inflammation takes longer to affect its function, and is deeper within the lid tissue and therefore farther away from the inflammatory virulence factors. It also has a narrow ductule compared to the lash follicle, and is constantly secreting meibum through this ductule, thereby preventing easy access for biofilm or virulence factors. After years of chronic and constant surface inflammation however, the gland is eventually penetrated and inflamed to the point of degraded performance.

Stage 3 DEBS occurs when the baseline aqueous component of the tear film is affected. The aqueous component of tears is produced by the Glands of Krauss and Wolfring as well as an accessory component of the lacrimal gland. These glands have their openings at the deeper fornices of the inner eyelids, much further from the inflammatory biofilm and virulence factors, and are 1,000 times or more, larger than the meibomian glands. Therefore, more years of chronic and constant exposure to the inflammatory components of blepharitis are necessary to finally degrade the production of aqueous tears. In clinical practice, the clinician will often see patients with Stage 2 meibomian disease, complaining of fluctuating vision, irritation, redness and tearing, watery eyes. Clinicians attempt to explain to these patients that they have a form of dry eye disease, with a deficient lipid layer leading to evaporative dry eye. When patients have watery teary eyes, this is many times a difficult explanation for patients to understand. What is interesting and informative, is that, excepting an autoimmune process such as Sjogren's disease, clinicians very seldom, if ever, see the opposite scenario, i.e. lots of lipids from healthy meibomian glands, but very few aqueous tears. Clinicians seldom, if ever, have to explain to a patient why they have oils running down their cheeks, but no watery tears. This is because the aqueous production cannot be affected until the meibomian glands have long since lost the fight against chronic inflammation and have effectively shut down. If aqueous insufficiency never occurs in isolation, but instead, almost always after meibomian disease, this makes it clear that it is not a different disease, but a later manifestation, or stage, of the same disease process.

Stage 4 DEBS involves the entire eyelid tissue and my include actual breakdown in the structural integrity of the eyelid leading to ectropion, entropion, floppy eyelid syndrome, and even sensory nerve destruction causing many patients to be asymptomatic in the face of advanced lid disease.

The novel concept of the Staged Disease explanation of DEBS described herein explains nearly every manifestation of inflammatory lid disease seen clinically, and makes understanding lid disease an easy concept. It also provides the framework for aspects of the invention, which addresses the underlying cause of DEBS, namely the biofilm accumulation. Embodiments of the present invention address shortcomings in the numerous blepharitis and dry eye treatments currently available by providing an easy pharmacological solution which inhibits the adherence and accumulation of biofilm along the lid margin. In particular, as discussed in greater detail below, in an embodiment, the method includes administering to a subject an effective amount of a biofilm inhibiting or disrupting compound to the eye or eyelid margin that inhibits, disrupts or disperses a biofilm along the margin of the eyelid. The eyelid margin is understood to include the margin of the eyelids that includes the eyelashes and the tissue within about 2 mm or 3 mm on either side of the lashes.

Bacteria live in either one of two states, planktonic vs within a biofilm. Bacteria in the planktonic state, i.e., individual free-floating bacteria, are more susceptible to attack from host defenses, antibiotics, or can be washed away more easily, than bacteria living within biofilms. Without being bound to any particular theory, inhibiting or dispersing a biofilm results in one or more of the following: removing biofilm accumulation, decreasing bacterial densities, reducing quorum-sensing, and avoiding or stopping the pathogenesis of dry eye and blepharitis since production of virulence factors is reduced or stopped.

Bacteria synthesize the protein/polysaccharide components of the biofilm. Bacteria also produce a class of proteins collectively termed "adhesins." These adhesins allow binding of bacterial cell surface components to either host cell surface components, or to an intermediary substrate which then binds to the host cell surface, or to components of extracellular biofilm matrix. Adhesins also promote binding of the biofilm to the host surface. Researchers have identified several adhesion proteins. Without being bound to a particular theory, one option for treating or preventing DEBS is inhibiting or disrupting the interaction of adhesin proteins with their respective receptors. Accordingly, an aspect of the invention is directed to treating DEBS by disrupting a biofilm on the eyelid margin by inhibiting the interaction adhesin proteins with adhesion protein receptors. Another aspect of the invention is directed to treating DEBS by disrupting a biofilm on the eyelid margin by disrupting the interaction adhesin proteins with adhesion protein receptors. Adhesin protein receptors are proteins and other biological molecules that include binding sites for adhesin proteins. For example, adhesin protein interactions with adhesin protein receptors with monoclonal antibodies (Mab) directed against adhesin proteins or their binding sites, or through compounds, such as small molecules that disrupt the interactions. In an embodiment, one or more compounds having biofilm inhibiting or disrupting properties are applied to eyelid surfaces in an amount effective to block or disrupt adhesin interaction with an adhesin protein receptor.

Exemplary adhesin proteins that may be targeted by embodiments of the invention are identified below. Embodiments of the invention may block the interaction of one or more adhesin proteins with one or more adhesin protein receptors. In an embodiment, the interaction of a single type of adhesin protein is blocked. In another embodiment, the interaction of a plurality of types of adhesin protein is blocked.

An exemplary adhesin protein interaction that may be blocked or disrupted in embodiments of the invention are interaction with polysaccharide intercellular adhesin. Polysaccharide intercellular adhesin (PIA) is significantly involved in biofilm accumulation and is produced by both *S. aureus* and *S. epidermidis*.

Another exemplary class of bacterial adhesin proteins is made up of proteins covalently anchored to bacterial cell peptidoglycans which specifically attach to the plasma or extracellular matrix (ECM) of the subject in need of treatment. These proteins are collectively referred to as microbial-surface-component-recognizing-adhesive-matrix-molecules (MSCRAMMs). MSCRAMMs recognize and bind to one or more components of the ECM, plasma, including collagens, fibrinogen (fibrinogen-binding protein, clumping factors A and B), fibronectin, elastin, laminin, bone sialoprotein, and for vitronectin.

Staph aureus surface protein G (SasG) is an exemplary adhesin protein known for a1 binding to the mucosa of the anterior nares and is likely involved in binding to mucosal tissue of the ocular adenexa as well, including lid margins and conjunctiva. In particular, SasG variants with eight, six and five repeats, formed biofilm. Several other variants do not.

Staphylococcal protein A (SpA) is another exemplary adhesin protein. Embodiments of the invention include an anti-SpA antibody, such as an anti-SpA monoclonal antibody (Mab), that would be beneficial in preventing adhesin protein activity. This antibody may be used alone or in conjunction with other antibodies, such as antibodies directed against binding targets for the SpA such as Mabs to clumping factor (Clf) A and B proteins.

An additional exemplary MSCRAMM adhesin protein in *S. epidermidis* is the fibrinogen-binding protein SdrG. Thus, embodiments of the invention include an antibody directed against SdrG, such as a monoclonal antibody, which would be beneficial in preventing adhesin protein interaction with adhesin protein receptors.

An additional exemplary MSCRAMM adhesin protein, SdrF, binds collagen. Thus, embodiments of the invention include an antibody directed against SdrF, such as a monoclonal antibody, which would be beneficial in preventing adhesin protein interaction with adhesin protein receptors.

An additional exemplary adhesin protein is Embp. Embp is a 1.1-MDa protein that can bind fibronectin. Studies by Christner and colleagues found that a 460-kDa isoform of Embp is capable of binding fibronectin which in turn can inhibit biofilm accumulation. Thus, embodiments of the invention include an antibody directed against Embp, such as a monoclonal antibody, which would be beneficial in preventing adhesin protein interaction with adhesin protein receptors.

Another exemplary adhesin protein are LPXTG motif-containing cell wall-anchored proteins termed *S. epidermidis* surface proteins, which have been implicated in biofilm production, specifically SesC. Polyclonal anti-SesC reduced the in vitro biofilm-forming and fibrinogen-binding, and therefore may be beneficial when added a topically administered medication. Thus, embodiments of the invention include an antibody directed against LPXTG motif-containing cell wall-anchored proteins such as SesC, such as a monoclonal antibody, which would be beneficial in preventing adhesin protein interaction with adhesin protein receptors.

*Staphylococcus aureus* collagen-binding protein is another exemplary cell surface adhesin. It has been shown that the topical application of a collagen-binding peptide before bacterial challenge decreased *S. aureus* adherence to de-epithelialized corneas. The collagen-binding adhesin is therefore involved in the pathogenesis of *S. aureus* infection of the cornea epithelium and may well be also involved in binding to the conjunctival epithelium of the lid margin, thus promoting biofilm formation. Human corneal epithelial cells (HCEC) adherence and invasion may be blocked by cytochalasin D and genistein, 2 potential adhesin blocking molecules. Thus, embodiments of the invention include at least one of cytochalasin D and genistein. Further embodiments of the invention include an antibody directed against *Staphylococcus aureus* collagen-binding protein, such as a monoclonal antibody, which would be beneficial in preventing adhesin protein interaction with adhesin protein receptors.

S. aureus fibronectin-binding protein (FnBP) may play the major role in bacterial adhesion along the lid margin and conjunctiva. Fibronectin is a glycoprotein found in the ECM and body fluids. It serves as a substrate for the adhesion of normal host cells, expressing the appropriate integrins, to one another. Bacteria have evolved to take advantage of the existence of fibronectin by producing fibronectin-binding proteins A and B (FnBPA and FnBPB) which cause a tight binding of the bacteria with the extracellular matrix (ECM). The current model for FnBP-mediated adhesion suggests a fibronectin-dependent bridging between S. aureus FnBPs and host cell α5β1 integrin. Fibronectin, found in human tears, increases in quantity with capillary dilation due to inflammation. It is likely that once bound using existing fibronectin as the bridge, the subsequent bacterial virulence factor-induced inflammation accelerates further exudation of fibronectin from the serum of dilated capillaries into the tears, providing more substrate for further binding and therefore biofilm accumulation, resulting in a vicious cycle. Competitive inhibition using anti-FnBP antibodies or FnBP-derived peptides should be effective in blocking receptor-ligand interactions at the conjunctival, or lid margin cell surface. In one study, S. aureus invasion was substantially but not completely eliminated by the absence of FnBP. Therefore, dry eye disease should be also substantially decreased by competitive binding of bacterial FnBP. FnBP also binds directly to a host cell surface protein, Heat shock Protein 60, so providing a Mab or a compound similar in action, to competitively bind the FnBP may effectively block two bacterial separate binding mechanisms. HSP 60 is a 57-kDa protein that was originally thought to be associated with the mitochondrial matrix, but is now known to be typical of eukaryotic cells and cytoplasmic membranes in general, so a HSP 60 Mab could be very effective along the surface of the lid margin and conjunctive or cornea.

The integrin protein has also been found to be a binding site for human lymphocytes invasion as well, when involved with host response inflammation, and is the basis for the mechanism of action for a patented novel dry eye product, a potent LFA-1/ICAM-1 antagonist SAR 1118 (Shire, Lifitegrast) U.S. Pat. Nos. 8,592,450 and 8,748,391 B2 which competitively binds the integrin protein, thus preventing binding and activation of lymphocytes. U.S. Pat. Nos. 8,748,391, 8,592,450, 9,085,553, 9,051,297 etc are for inhibiting Lymphocyte Function-associated Antigen-1, in an effort to reduce inflammation by shutting down white cell responses to inflammatory factors (virulence factors). The present invention does not shut down white cells by blocking integrin, rather, embodiment of the present invention shut down the formation of biofilms by blocking adhesins, thus inhibiting the buildup of bacteria, thus inhibiting the quorum sensing gene activation of virulence factors.

Another exemplary adhesin is a staphylococcal 145 kDa cell wall adhesin, originally found in bovine mastitis, which allows Staph to bind to epithelial cells. Antibodies against the 145 kDa adhesin protein were found to block bacterial adhesion to bovine epithelial cells as well as rat intestinal epithelial cells. This adhesin may also play a role in binding staph to human epithelial cells in moist environs such as the lid margin.

It is well known that S. epidemidis is easily adherent to contact lenses. Strain variability in terms of exopolysaccharide expression, adhesion expression and the solution used for lens immersion were the primary determinant of adherence and colonization of contact lens, more so than the properties of the lenses themselves. Blocking or reducing the adhesin molecule may also play a large role in preventing contact lens intolerance and dry eye in these patients and this application of adhesin protein interaction inhibiting or disrupting compounds may also be useful in embodiments of the present invention. In S. epidermidis, bacterial proteins can be bifunctional adhesins/autolysins AtlE and AAe. These proteins have specific adherence functions (by bindin noncovalently to vitronectin), and may also function to release eDNA, which is an important adherence/aggregation factor in both S. aureus and S. epidermidis biofilm formation. Mabs to AtlE and Aae, such as monoclonal antibodies, may be included in embodiments of the invention to reduce adherence and formation of biofilms.

For pathology and virulence to occur, factors must exist that not only allow adherence of bacteria to ECM or host cell surfaces, but also allow for accumulation of the biofilm mass, within which the bacteria can increase their densities to quorum-sensing levels. Known adhesins allowing for biofilm accumulation (biofilm sticking to biofilm) are produced by S. epidermidis (and to some extent S. aureus) are polysaccharide intercellular adhesin (PIA) and accumulation associated protein (Aap). Antibodies, such as monoclonal antibodies, or compounds blocking these adhesin should prevent accumulation of biofilm mass, thereby significantly decreasing the incidence of dry eye disease.

Another effective mechanism of blocking adhesins could be the addition of actin microfilament inhibitor cytochalasin D (0.5 μg/ml; Sigma) or the tyrosine kinase inhibitor genistein (250 μg/ml; Calbiochem) which have been shown to reduced the binding and subsequent internalization of S. aureus by >99.9%. Thus embodiments of the invention include one or both of these compounds.

In another aspect of this invention, since a monoclonal antibody (MAb) specific for β1 integrins dramatically reduced S. aureus adherence and invasion, addition of a β1Mab should prevent the formation of a Fn bridge linking the host cell β1 integrin and the FnBP adhesin.

In another embodiment of the invention, addition of a MAb specific for eukaryotic Hsp60, Hsp60 MAb, should also significantly reduce the binding of S. aureus. Combined, these 2 Mabs could block the multifunctional adhesin FnBP from binding directly to both host cell ligands, Hsp60 and β1 integrins. Du-D4 is the functional fragment of FnBP, therefore, a Du-D4 antiserum also blocks the association of Hsp60 with the bacterial cell surface and thus may be an effective adhesin inhibitor.

Fibronectin itself could serve as an adhesin blocker in high concentrations. This effect would be consistent with the function of Fn as a bifunctional molecule in which a blocking effect at high concentrations would be due to saturation of the integrin-FnBP system.

Delmoprinol is a morpholino compound that has been demonstrated to have utility in a3 the treatment of the oral cavity, especially tooth surface, and for the removal or inhibition of dental plaque, which is a biofilm. The compound and its manufacture are disclosed in U.S. Pat. No. 4,894,221, the contents of which are incorporated herein by reference in their entirety. Delmopinol, and its derivatives, may be used to prevent biofilm formation along the eyelid margin. In an embodiment, delmopinol may work more effectively when formulated with a bacterial adhesin peptide, e.g. p1025, or an antibody that binds to a bacterial adhesin peptide. Thus, delmopinol may act as an augmentation agent in any of proposed adhesion inhibitors described herein.

Extracellular polysaccharides can also act as adhesins. Exemplary extracellular polysaccharides include PS/A, PNSG and PNAG and the aforementioned PIA. Embodiments of the invention include blocking the activity of one or more of the identified adhesin proteins to thereby reducing the biofilm accumulation.

The following biofilm inhibiting or disrupting blocking compounds block or disrupt adhesin protein interaction with adhesin protein receptors, which may be used individually or in combination, may be obtained from Inhibitex, Inc., Alpharetta, Ga., USA: S. aureus Clf40 (N1 N2N3)—full length A domain of Clumping factor A (amino acids (AA) 40-559); S. aureus Clf41 (N2N3)—post protease site fragment of Clf 40 (AA 223-559); S. epidermidis SdrG (N1 N2N3)—full length A domain of SdrG (AA 50-597); S. epidermidis SdrG (N2N3)—post protease site fragment of SdrG (AA 273-597).

An additional biofilm inhibiting or disrupting compounds that may be included, individually or combination with each other or other biofilm inhibiting or disrupting compounds, in embodiments of the invention are thymosin β4 (or Tβ4), which is available from G-TreeBNT, lactoferrin, xylitol, mangainin I covalently linked to II-mercapto undecanoic acid and 6-mercaptohexanol in 1:3 ratio, Fraction 7 from Terminalia chebula or its Gallic acid, cis-2-decenoic acid, cytochalasin D, genistein (tyrosine kinase inhibitor), norspermidine, polyamines (alone or in synergistic combination with D-amino acids), alginate lyase, N-acetyl-hearosan lyase, hyaluronidase enzymes, sulphathiazole (suphonamide), iron chelating agents (alone or in combination with aminoglycosides), N-acetyl cysteine, D-amino acids, disperin B, DNase I, furanone, S-phenyl-1-cysteine sulphoxide and the derivative compound diphenyl disulfide.

In embodiments of the invention, biofilm inhibiting or disrupting compounds are administered to the eye lid margin in an amount effective to disrupt biofilm formation. The biofilm inhibiting or disrupting compounds may be administered topically. In an embodiment, the biofilm inhibiting or disrupting compounds are administered in as an eye drop. In another embodiment, the biofilm inhibiting or disrupting compounds are administered as a gel or cream directly to the eyelid margin, such as with a finger tip or swab.

The biofilm inhibiting or disrupting compounds are administered in a dose effective to inhibit adhesin protein interaction with adhesin protein receptors and to disrupt a biofilm on the eyelid margin of the subject. An effective dose is a dose at which biofilm formation is disrupted.

The biofilm inhibiting or disrupting compounds are administered for a duration sufficient to relieve the symptoms of DEBS for the subject being treated. In an embodiment, the duration is at least once daily treatment of the effective dose for a duration of one day to one month. In another embodiment, the duration is administered over longer periods of time to prevent the formation of new biofilms on the eyelid margin of the subject. In embodiments, the dose is administered on a different schedule, such as multiple times a day or weekly.

In embodiments of the invention, the at least one biofilm inhibiting or disrupting compound is an antibody or antibody fragment against a protein selected from the group consisting of Staphylococcal protein A (SpA), clumping factor A, clumping factor B, fibrinogen-binding protein SdrG, fibrinogen-binding protein SdrF, S. epidermidis Extracellular Motif Binding Protein (Embp), LPXTG motif-containing S. epidermidis surface protein SesC, S. aureus collagen-binding protein, S. aureus fibronectin-binding protein, S. aureus fibronectin-binding protein A, S. aureus fibronectin-binding protein B, Heat Shock Protein 60, staphylococcal 145 kDa cell wall adhesin, S. epidermidis AtlE, S. epidermidis Aae, S. epidermidis AtlE, S. epidermidis Aae, S. epidermidis polysaccharide intercellular adhesin, S. aureus polysaccharide intercellular adhesin, β1 integrin, and combinations thereof, and further wherein, the antibody is capable of blocking the activity of adhesin protein in biofilm formation.

In embodiments of the invention, the at least one biofilm inhibiting or disrupting compound is selected from the group consisting of cytochalasin D, genistein, SAR 1118, fibronectin, delmopinol, S. aureus Clf40 (N1 N2N3), S. aureus Clf41 (N2N3), S. epidermidis SdrG (N1 N2N3), S. epidermidis SdrG (AA 50-597), S. epidermidis SdrG (N2N3), thymosin β4, lactoferrin, xylitol, mangainin I covalently linked to II-mercapto undecanoic acid and 6-mercaptohexanol in 1:3 ratio, Fraction 7 from Terminalia chebula or its Gallic acid, cis-2-decenoic acid, norspermidine, polyamines, alginate lyase, N-acetyl-hearosan lyase, hyaluronidase enzymes, sulphathiazole, iron chelating agents, N-acetyl cysteine, D-amino acids, disperin B, DNase I, furanone, S-phenyl-1-cysteine, sulphoxide, diphenyl disulfide, FnBP-derived peptides, and combinations thereof.

The biofilm inhibiting or disrupting compounds may be administered in formulations that include additional excipients and solvents as are known in the art for use in compounds being applied to the eye or eyelid margin. For example, the formulations may include one or more of the following: balanced salt solutions, water, gelling solutions, and stabilizers.

In embodiments of the invention, the biofilm inhibiting or disrupting compounds may be combined with other therapeutic agents, such as antibacterial agents and anti-inflammatory agents.

Embodiments of the invention may include a pretreatment in which the biofilm is removed from the eyelid margin prior to administration of the adhesin protein activity blocking compounds. An example of a pretreatment is described in U.S. Pat. No. 9,039,729, the disclosures of which are incorporated herein in their entirety.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. The invention in its broader aspects is, therefore, not limited to the specific details, representative apparatus and method, and illustrative examples shown and described. Accordingly, departures may be made from such details without departing from the spirit or scope of the general inventive concept.

What is claimed is:

1. A method of treating Dry Eye and Blepharitis Syndrome (DEBS) in a subject comprising administering to the eyelid margin of the subject a dose of at least one biofilm inhibiting or disrupting compound in a dose sufficient to disrupt a biofilm on the eyelid margin or to disperse a biofilm already formed on the eyelid margin.

2. The method of claim 1, wherein the at least one biofilm inhibiting compound is selected from a protein, protein fragment, an antibody, and a small molecule.

3. The method of claim 1 wherein the at least one biofilm inhibiting or disrupting compound binds to an adhesin protein.

4. The method of claim 1, wherein the at least one biofilm inhibiting or disrupting compound binds to a receptor for an adhesin protein.

5. The method of claim 1, wherein the at least one biofilm inhibiting or disrupting compound is an antibody or antibody fragment against a protein selected from the group consisting of Staphylococcal protein A (SpA), clumping factor A, clumping factor B, fibrinogen-binding protein SdrG, fibrinogen-binding protein SdrF, *S. epidermidis* Extracellular Motif Binding Protein (Embp), LPXTG motif-containing *S. epidermidis* surface protein SesC, *S. aureus* collagen-binding protein, *S. aureus* fibronectin-binding protein, *S. aureus* fibronectin-binding protein A, *S. aureus* fibronectin-binding protein B, Heat Shock Protein 60, staphylococcal 145 kDa cell wall adhesin, *S. epidermidis* AtlE, *S. epidermidis* Aae, *S. epidermidis* AtlE, *S. epidermidis* Aae, *S. epidermidis* polysaccharide intercellular adhesin, *S. aureus* polysaccharide intercellular adhesin, β1 integrin, and combinations thereof, and further wherein, the antibody is capable of blocking the activity of adhesin protein in biofilm formation.

\* \* \* \* \*

UNITED STATES PATENT AND TRADEMARK OFFICE
CERTIFICATE OF CORRECTION

PATENT NO.       : 10,799,447 B2
APPLICATION NO.  : 16/082151
DATED            : October 13, 2020
INVENTOR(S)      : James M. Rynerson It is certified that error appears in the above-identified patent and that said Letters Patent is hereby corrected as shown below:

In the Specification

Column 1, Lines 8-9, "compositions for treating an eye disorder, and more particularly," should be --compositions for treating an eye disorder and, more particularly,--.

Column 1, Line 24, "eye disorder in the world, and unfortunately," should be --eye disorder in the world and, unfortunately,--.

Column 2, Line 35, "based a better understanding" should be --based on a better understanding--.

Column 3, Line 7, "factors that are primarily responsible for" should be --factors are primarily responsible for--.

Column 4, Lines 47-48, "my include" should be --may include--.

Column 5, Lines 55-56, "are interaction with" should be --is interaction with--.

Column 6, Line 4, "*Staph aureus*" should be --*Staphylococcus aureus*--.

Column 6, Line 41, "protein are" should be --protein is--.

Column 7, Line 52, "embodiment" should be --embodiments--.

Column 7, Line 58, "Staph" should be --Staphylococcus--.

Column 7, Line 62, "staph" should be --*Staphylococcus*--.

Column 8, Lines 9-10, "(by bindin noncoavalently" should be --(by binding noncovalently--.

Column 8, Line 32, "to reduced the binding" should be --to reduce the binding--.

Signed and Sealed this
Twenty-second Day of December, 2020

Andrei Iancu
*Director of the United States Patent and Trademark Office*

CERTIFICATE OF CORRECTION (continued)
U.S. Pat. No. 10,799,447 B2

Column 8, Line 54, "Delmoprinol" should be --Delmopinol--.

Column 9, Lines 5-6, "thereby reducing" should be --thereby reduce--.

Column 9, Lines 18-19, "An additional biofilm inhibiting or disrupting compounds that may be included, individually or combination with each" should be --Additional biofilm inhibiting or disrupting compounds that may be included, individually or in combination with each--.

Column 9, Line 39, "compounds are administered in as an eye drop." should be --compounds are administered as an eye drop.--.

In the Claims

Column 10, Line 56 (Claim 1), "inhibiting or disrupting compound in a dose sufficient to" should be --inhibiting compound in a dose sufficient to--.

Column 10, Lines 63-64 (Claim 3), "inhibiting or disrupting compound binds to an adhesin protein." should be --inhibiting compound binds to an adhesin protein.--.

Column 10, Line 66-67 (Claim 4), "inhibiting or disrupting compound binds to a receptor for an adhesin protein." should be --inhibiting compound binds to a receptor for an adhesin protein.--.

Column 11, Line 2 (Claim 5), "inhibiting or disrupting compound is an antibody" should be --inhibiting compound is an antibody--.

Column 11, Lines 12-15 (Claim 5), "staphylococcal 145-kDa cell wall adhesin, *S. epidermidis* AtlE, *S. epidermidis* Aae, *S. epidermidis* AtlE, *S. epidermidis* Aae, *S. epidermidis* polysaccharide intercellular adhesin," should be --staphylococcal 145-kDa cell wall adhesin, *S. epidermidis* AtlE, *S. epidermidis* Aae, *S. epidermidis* polysaccharide intercellular adhesin,--.